(12) United States Patent
Takashino et al.

(10) Patent No.: US 9,949,781 B2
(45) Date of Patent: Apr. 24, 2018

(54) GRASPING TREATMENT UNIT, GRASPING TREATMENT INSTRUMENT, AND GRASPING TREATMENT SYSTEM

(71) Applicant: OLYMPUS CORPORATION, Hachioji-shi, Tokyo (JP)

(72) Inventors: Tomoyuki Takashino, Fuchu (JP); Yusuke Takei, Hino (JP); Kazuhiro Tanaka, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/279,137

(22) Filed: Sep. 28, 2016

(65) Prior Publication Data
US 2017/0014175 A1 Jan. 19, 2017

Related U.S. Application Data

(63) Continuation of application No. PCT/JP2015/070886, filed on Jul. 22, 2015.

(30) Foreign Application Priority Data

Sep. 5, 2014 (JP) ................. 2014-181414

(51) Int. Cl.
*A61B 18/08* (2006.01)
*A61B 18/12* (2006.01)
(Continued)

(52) U.S. Cl.
CPC ............ *A61B 18/085* (2013.01); *A61B 18/10* (2013.01); *A61B 18/12* (2013.01); *A61B 2018/00601* (2013.01)

(58) Field of Classification Search
CPC ....... A61B 18/085; A61B 18/10; A61B 18/12; A61B 2018/1452; A61B 2018/1455;
(Continued)

(56) References Cited

U.S. PATENT DOCUMENTS 4,527,560 A   7/1985 Masreliez

FOREIGN PATENT DOCUMENTS

EP   2 535 013 A1   12/2012
JP   H02-59356 A    2/1990
(Continued)

OTHER PUBLICATIONS

Oct. 27, 2015 International Search Report issued in International Patent Application No. PCT/JP2015/070886.
(Continued)

*Primary Examiner* — Michael Peffley
*Assistant Examiner* — Samantha Good
(74) *Attorney, Agent, or Firm* — Oliff PLC

(57) ABSTRACT

A grasping treatment unit includes a first jaw, and a second jaw openable and closable relative to the first jaw. In the first jaw, a heating wire continues without branching from a first extending end to a second extending end, and heat is generated over an entire length from the first extending end to the second extending end when the electric current flows through the heating wire. In a heating portion, a calorific value per unit area is higher in a distal portion than in a proximal portion in the first jaw when the heat is generated from the heating wire. On a treatment surface of the first jaw, an amount of heat transfer from the heating portion is greater in the distal portion than in the proximal portion.

12 Claims, 9 Drawing Sheets

(51) Int. Cl.
*A61B 18/10* (2006.01)
*A61B 18/00* (2006.01)

(58) Field of Classification Search
CPC .... A61B 2018/1442; A61B 2018/1445; A61B 2018/1447
See application file for complete search history.

(56) References Cited

FOREIGN PATENT DOCUMENTS

| JP | H08-250266 A | 9/1996 |
|----|--------------|--------|
| JP | 2001-198137 A | 7/2001 |
| JP | 2004-188012 A | 7/2004 |
| JP | 2008-503290 A | 2/2008 |
| JP | 2012-161565 A | 8/2012 |
| JP | 2014-144183 A | 8/2014 |

OTHER PUBLICATIONS

Mar. 16, 2017 International Preliminary Report on Patentability issued in PCT/JP2015/070886.

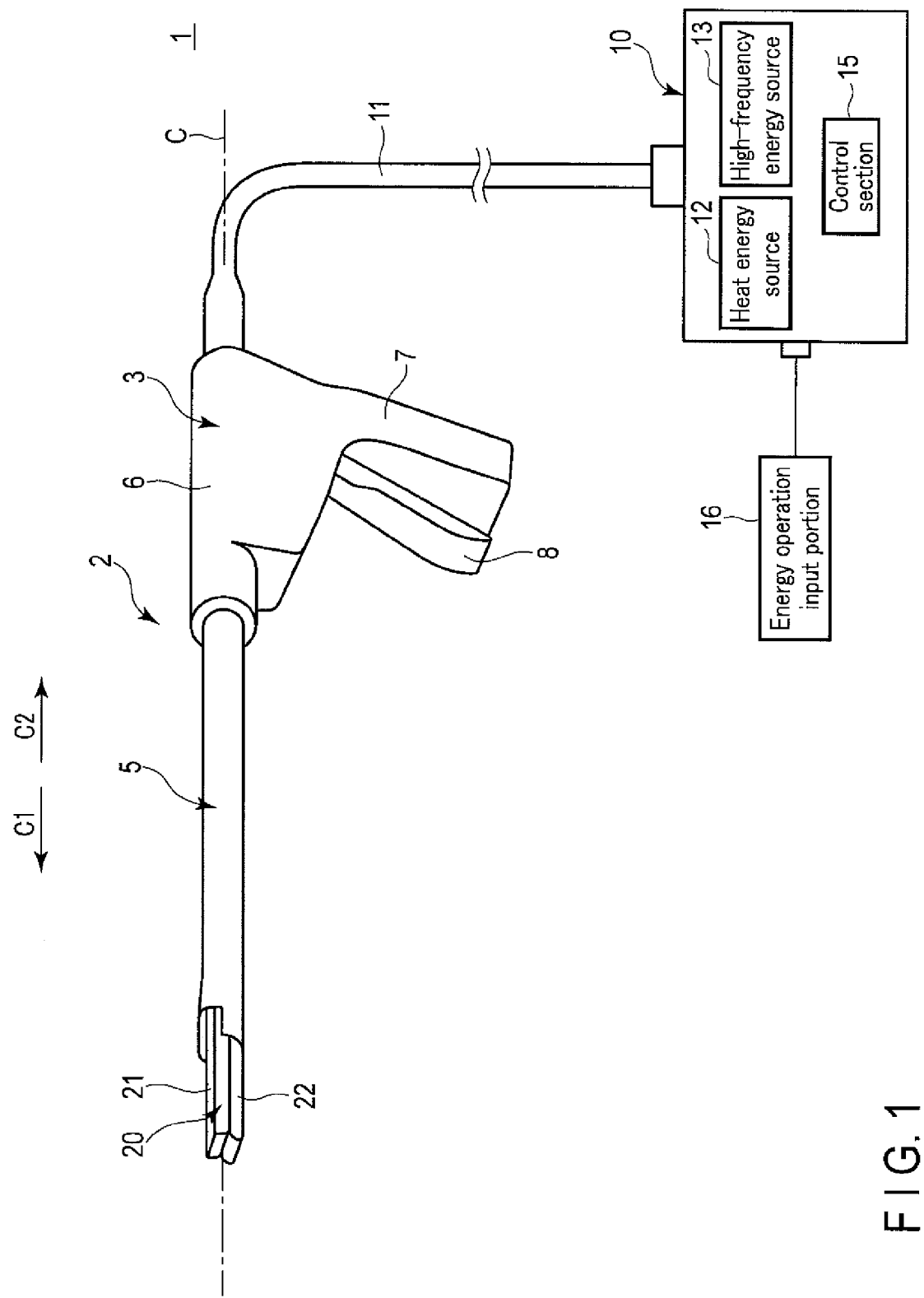
F I G. 1

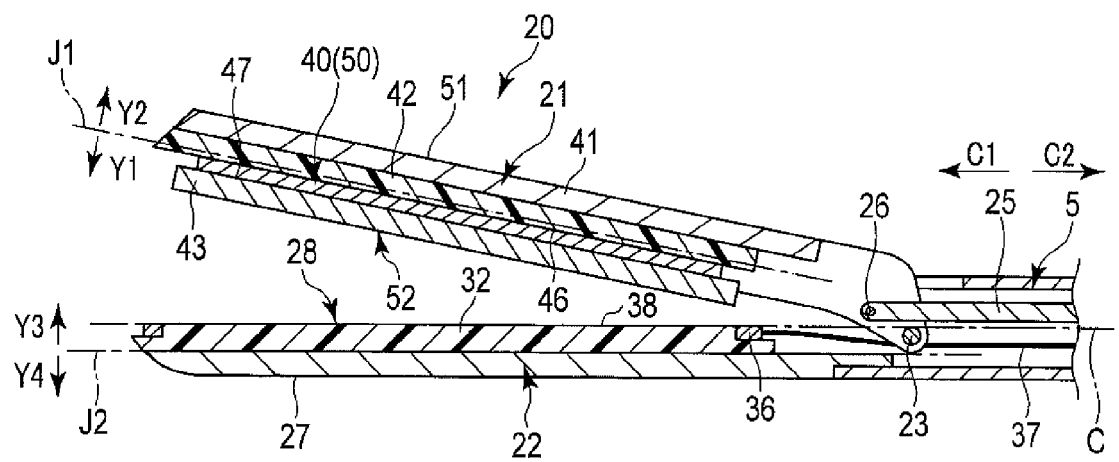
F I G. 2
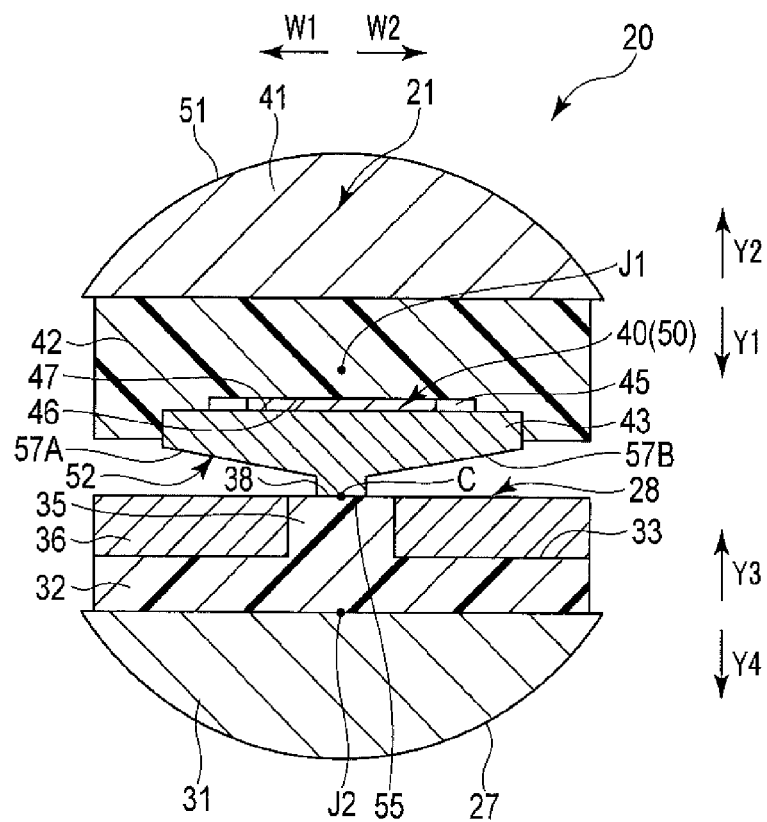
F I G. 3

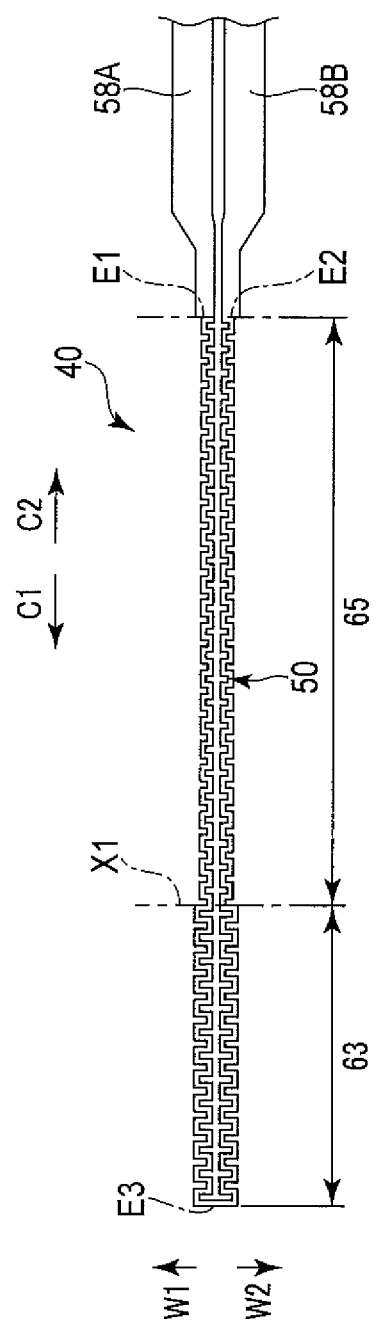
F I G. 8

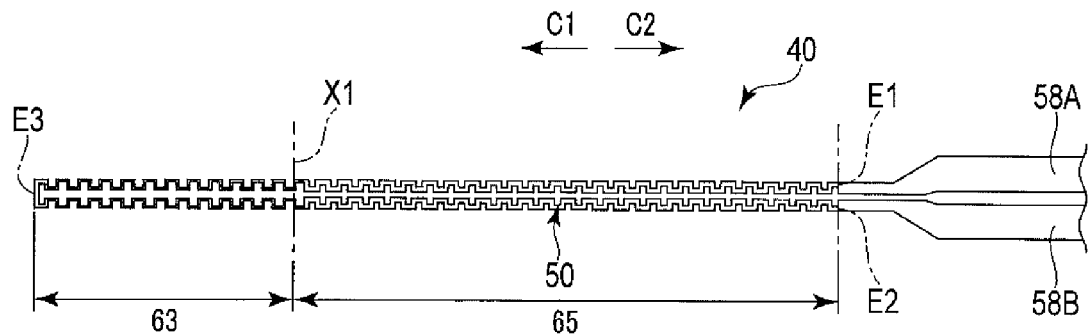
F I G. 11
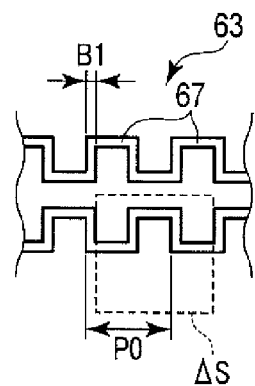
F I G. 12
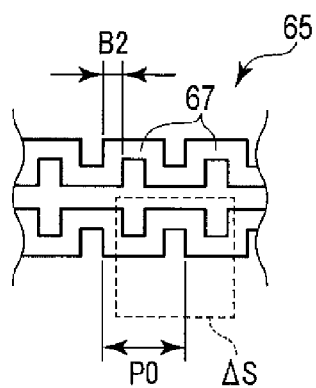
F I G. 13

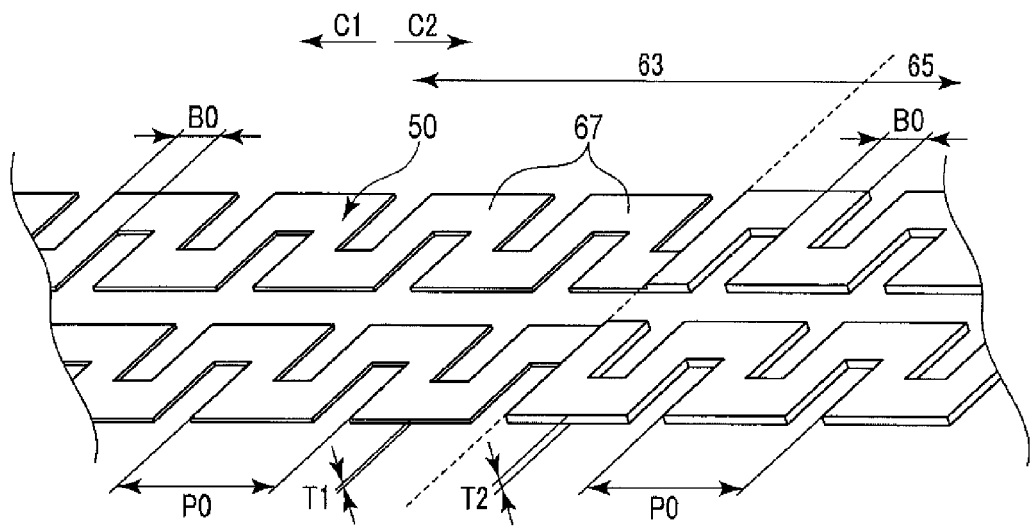
F I G. 14
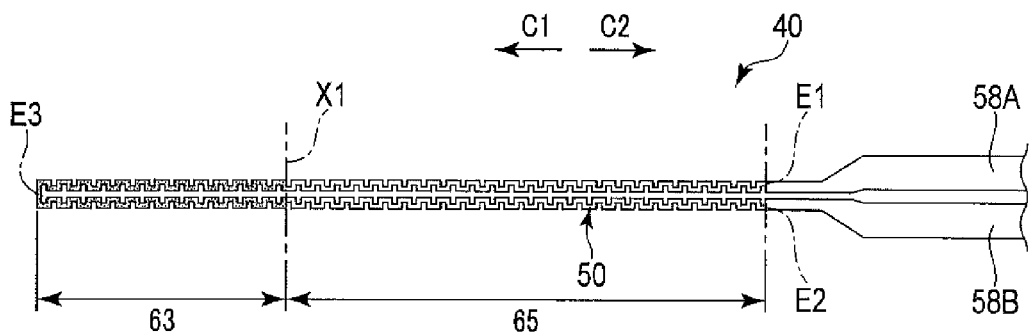
F I G. 15
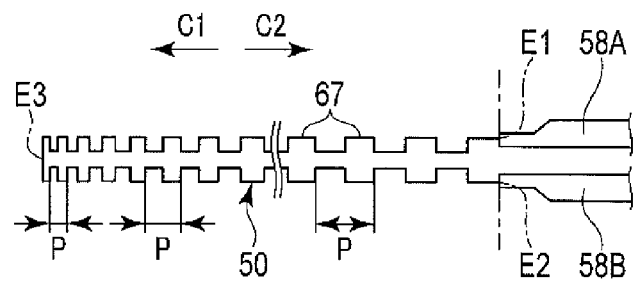
F I G. 16

GRASPING TREATMENT UNIT, GRASPING TREATMENT INSTRUMENT, AND GRASPING TREATMENT SYSTEM

CROSS-REFERENCE TO RELATED APPLICATIONS

This is a Continuation application of PCT Application No. PCT/JP2015/070886, filed Jul. 22, 2015 and based upon and claiming the benefit of priority from prior Japanese Patent Application No. 2014-181414, filed Sep. 5, 2014, the entire contents of which are incorporated herein by reference.

BACKGROUND OF THE INVENTION

1. Field of the Invention

The present invention relates to a grasping treatment unit configured to treat a grasped treated target by use of heat generated in a heating portion (heating element). The present invention also relates to a grasping treatment instrument and a grasping treatment system including the grasping treatment unit.

2. Description of the Related Art

Jpn. Pat. Appln. KOKAI Publication No. 2012-161565 discloses a grasping treatment instrument which grasps a treated target between two jaws (grasping portions). In this grasping treatment instrument, the space between the jaws is openable and closable, and more than one heating elements (heating wires) are provided in one of the jaws. The treated target grasped between the jaws is treated by use of heat generated in the heating elements (heating portions). A temperature measurement chip as a temperature detection section is provided in the jaw in which the heating elements are provided. The temperature in the jaw provided with the heating elements is detected by the temperature measurement chip. A calorific value in the heating elements is adjusted on the basis of the detection result in the temperature measurement chip.

BRIEF SUMMARY OF THE INVENTION

According to one aspect of the invention, a grasping treatment unit configured to grasp and treat a living tissue, the grasping treatment unit including: a first jaw which extends from a proximal portion toward a distal portion, and which has an outer surface exposed to an outside; a second jaw which extends from a proximal portion toward a distal portion, and which is openable and closable relative to the first jaw; a heating portion including a heating wire, the heating wire being disposed in a range from the proximal portion to the distal portion in the first jaw, continuing without branching from a first extending end which is one end to a second extending end which is the other end in an extending direction, and being configured to generate heat over an entire length from the first extending end to the second extending end when an electric current flows therethrough, the heating portion being higher in calorific value per unit area in the distal portion than in the proximal portion in the first jaw in a state where the heat is generated from the heating wire; and a treatment surface which is provided on the outer surface of the first jaw, and which faces the second jaw, the treatment surface being configured to treat the living tissue in a state where an amount of heat transfer from the heating portion to the treatment surface is greater in the distal portion than in the proximal portion.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 1 is a schematic diagram showing a grasping treatment system according to a first embodiment;

FIG. 2 is a sectional view schematically showing the configuration of the distal portion of a grasping treatment instrument including a grasping treatment unit according to the first embodiment in a state where the space between a first jaw and a second jaw is open;

FIG. 3 is a sectional view schematically showing the first jaw and the second jaw according to the first embodiment in a section perpendicular to a longitudinal axis;

FIG. 8 is a schematic diagram showing the configuration of the heating wire according to a first modification;

FIG. 11 is a schematic diagram showing the configuration of the heating wire according to a second modification;

FIG. 12 is a schematic diagram showing an extending state of the heating wire according to the second modification in the first heating region;

FIG. 13 a schematic diagram showing an extending state of the heating wire according to the second modification in the second heating region;

FIG. 14 is a schematic diagram showing the configuration of the heating wire according to a third modification;

FIG. 15 is a schematic diagram showing the configuration of the heating wire according to a fourth modification;

FIG. 16 is a schematic diagram showing the configuration of the heating wire according to a fifth modification;

DETAILED DESCRIPTION OF THE INVENTION

First Embodiment

Figure 4:
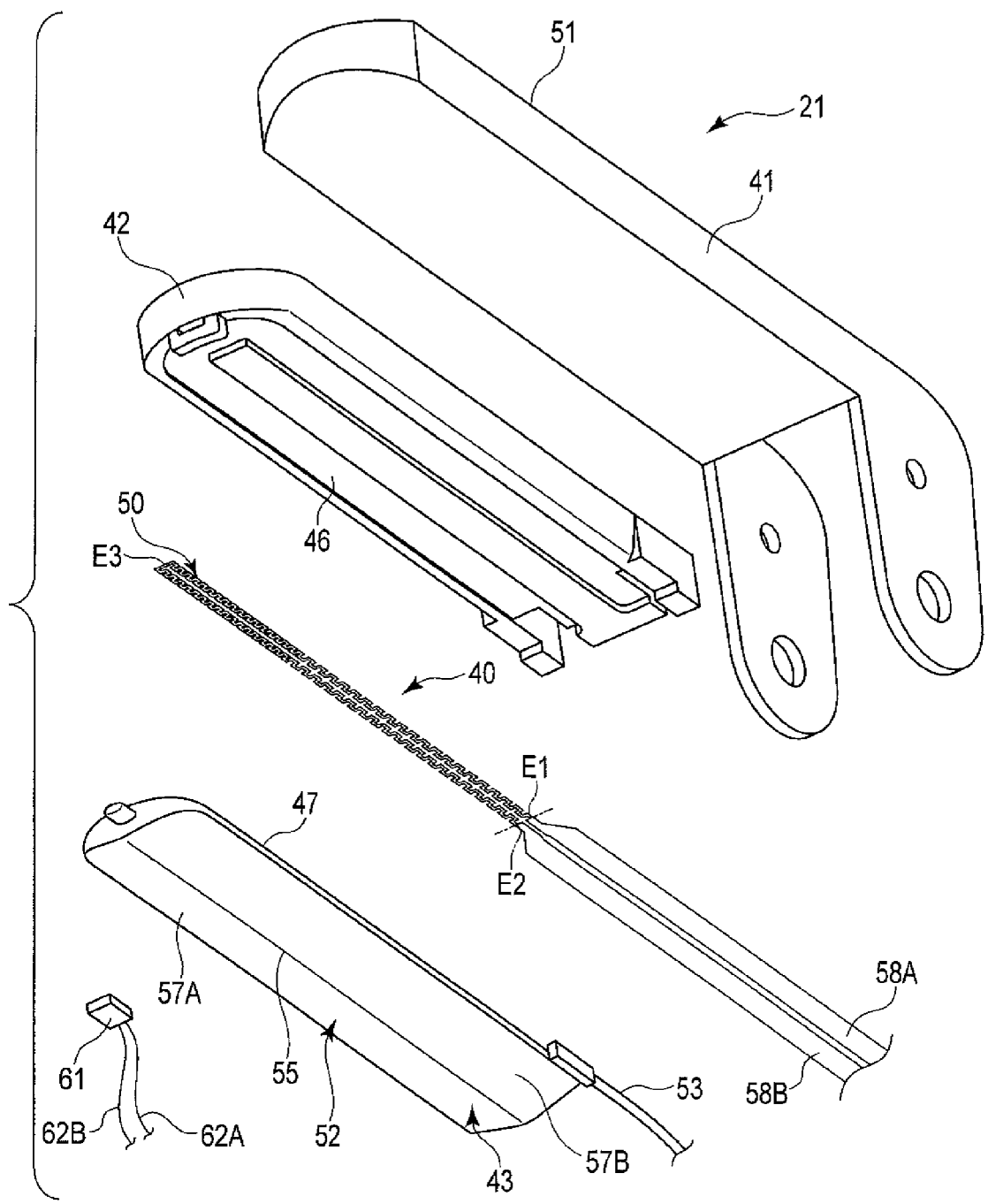
FIG. 4 is a perspective view schematically showing the configuration of the second jaw according to the first embodiment that is disassembled into components.

A first embodiment of the present invention will be described with reference to FIG. 1 to FIG. 7.

FIG. 1 is a diagram showing a grasping treatment system 1. As shown in FIG. 1, the grasping treatment system 1 includes a grasping treatment instrument 2. The grasping treatment instrument 2 has a longitudinal axis C. Here, one of two directions parallel to the longitudinal axis C is a distal direction (direction of an arrow C1 in FIG. 1), and the direction opposite to the distal direction is a proximal direction (direction of an arrow C2 in FIG. 1). In the present embodiment, the grasping treatment instrument 2 is a heat treatment instrument configured to treat a treated target such as a living tissue by using heat as energy, and is also a high-frequency treatment instrument configured to treat the treated target by using high-frequency electric power (high-frequency current).

The grasping treatment instrument 2 includes a holding unit (handle unit) 3, and a cylindrical shaft (sheath) 5 which is coupled to the distal direction side of the holding unit 3. In the present embodiment, the central axis of the shaft 5 is the longitudinal axis C. The holding unit 3 includes a cylindrical case portion 6 extending along the longitudinal axis C, and a fixed handle 7 extending from the cylindrical case portion 6 in a certain direction that intersects with the longitudinal axis C. In the present embodiment, the cylindrical case portion 6 is provided coaxially with the shaft 5, and the shaft 5 is inserted into an inside of the cylindrical case portion 6 from the distal direction side and thereby attached to the holding unit 3. The fixed handle 7 is formed integrally with the cylindrical case portion 6. The holding unit 3 includes a movable handle 8 which is rotatably attached to the cylindrical case portion 6. The movable handle 8 is rotated relative to the cylindrical case portion 6, and the movable handle 8 thereby performs an open or close motion relative to the fixed handle 7.

One end of a cable 11 is connected to the holding unit 3 (the cylindrical case portion 6). The grasping treatment system 1 includes an energy source unit 10 which is, for example, an electric power generator. The other end of the cable 11 is connected to the energy source unit 10. In the present embodiment, the energy source unit 10 includes a heat energy source (energy source) 12, a high-frequency energy source 13, and a control section 15. The heat energy source 12 and the high-frequency energy source 13 are, for example, output circuits configured to output electric energy. The control section 15 is formed from, for example, a processor including a central processing unit (CPU) or an application specific integrated circuit (ASIC). The energy source unit 10 is electrically connected to an energy operation input portion 16 such as a foot switch.

A grasping treatment unit 20 is coupled to the distal direction side of the shaft 5. The grasping treatment unit 20 includes a first jaw 21 which is a first grasping portion, and a second jaw 22 which is a second grasping portion. In the grasping treatment unit 20, the space between the first jaw 21 and the second jaw 22 is openable and closable. That is, the first jaw 21 and the second jaw 22 are openable and closable relative to each other.

FIG. 2 is a diagram showing the configuration of the distal portion of the grasping treatment instrument 2 including the grasping treatment unit 20. FIG. 2 shows a state where the space between the first jaw 21 and the second jaw 22 is open. FIG. 3 is a diagram showing the first jaw 21 and the second jaw 22 in a section perpendicular to the longitudinal axis C. FIG. 3 shows a state where the space between the first jaw 21 and the second jaw 22 is closed.

As shown in FIG. 2 and FIG. 3, the first jaw 21 has a first jaw axis J1. The first jaw axis J1 is the central axis of the first jaw 21, and the first jaw (first grasping portion) 21 extends along the first jaw axis J1 from the proximal portion toward the distal portion. Here, two directions parallel to the first jaw axis J1 are jaw longitudinal directions (first jaw longitudinal directions) of the first jaw 21. One of the jaw longitudinal directions (longitudinal directions) is a jaw distal direction (first jaw distal direction) of the first jaw 21, and the direction opposite to the jaw distal direction (first jaw distal direction) is a jaw proximal direction (first jaw proximal direction) of the first jaw 21. The jaw distal direction of the first jaw 21 corresponds to a direction toward the distal portion in the first jaw 21, and the jaw proximal direction of the first jaw 21 corresponds to a direction toward the proximal portion in the first jaw 21.

The second jaw 22 has a second jaw axis J2. The second jaw axis J2 is the central axis of the second jaw 22, and the second jaw (second grasping portion) 22 extends along the second jaw axis J2 from the proximal portion toward the distal portion. Here, two directions parallel to the second jaw axis J2 are jaw longitudinal directions (second jaw longitudinal directions) of the second jaw 22. One of the jaw longitudinal directions (longitudinal directions) is a jaw distal direction (second jaw distal direction) of the second jaw 22, and the direction opposite to the jaw distal direction (second jaw distal direction) is a jaw proximal direction (second jaw proximal direction) of the second jaw 22. The jaw distal direction of the second jaw 22 corresponds to a direction toward the distal portion in the second jaw 22, and the jaw proximal direction of the second jaw 22 corresponds to a direction toward the proximal portion in the second jaw 22.

In the present embodiment, the second jaw 22 is fixed to the shaft 5 in the distal portion of the shaft 5. The second jaw axis J2 is substantially parallel to the longitudinal axis C of the shaft 5. The first jaw 21 is attached to the distal portion of the shaft 5 via a support pin 23. The first jaw 21 is rotatable relative to the shaft 5 around the support pin 23. A rod 25 extends from the proximal direction side toward the distal direction side inside the shaft 5. The rod 25 is movable relative to the shaft 5 along the longitudinal axis C. The proximal portion of the rod 25 is coupled to the movable handle 8 inside the cylindrical case portion 6. The distal portion of the rod 25 is connected to the first jaw 21 via a connection pin 26. The movable handle 8 is opened or closed relative to the fixed handle 7, and the rod 25 is thereby moved relative to the shaft 5 along the longitudinal axis C. As a result, the first jaw 21 rotates relative to the shaft 5, and the first jaw 21 performs open or close motion relative to the second jaw 22. In this instance, the second jaw 22 opens or closes relative to the first jaw 21 because the second jaw 22 is fixed to the shaft 5. That is, the space between the first jaw 21 and the second jaw 22 opens or closes in the grasping treatment unit 20 due to the movement of the rod 25 relative to the shaft 5. Therefore, the movable handle 8 is an open-or-close operation input portion configured to input an open-or-close operation to open or close the space between the first jaw (first grasping portion) 21 and the second jaw (second grasping portion) 22.

Here, a direction toward the second jaw 22 in the first jaw 21 is a close direction (direction of an arrow Y1 in FIG. 2 and FIG. 3) of the first jaw 21, and the direction away from the second jaw 22 in the first jaw 21 is a jaw open direction (direction of an arrow Y2 in FIG. 2 and FIG. 3) of the first jaw 21. The jaw close direction (first jaw close direction) of the first jaw 21 is one direction that intersects with (perpendicular to) the first jaw axis J1, and the jaw open direction (first jaw open direction) of the first jaw 21 is a direction opposite to the jaw close direction. A direction toward the first jaw 21 in the second jaw 22 is a jaw close direction (direction of an arrow Y3 in FIG. 2 and FIG. 3) of the second jaw 22, and the direction away from the first jaw 21 in the second jaw 22 is a jaw open direction (direction of an arrow Y4 in FIG. 2 and FIG. 3) of the second jaw 22. The jaw close direction (second jaw close direction) of the second jaw 22 is one direction intersecting with (perpendicular to) the second jaw axis J2, and the jaw open direction (second jaw open direction) of the second jaw 22 is a direction opposite to the jaw close direction. Two directions intersecting with (perpendicular to) the first jaw axis J1 and perpendicular to the jaw open direction and the jaw close direction of the first jaw 21 are jaw width directions (directions of an arrow W1 and an arrow W2 in FIG. 3). The jaw width directions are directions intersecting with (perpendicular to) the second jaw axis J2 and perpendicular to the jaw open direction and the jaw close direction of the second jaw 22.

The second jaw 22 includes a support member (second support member) 31 fixed to the shaft 5, and a receiving member 32 fixed to the support member 31. The support member 31 and the receiving member 32 extend along the second jaw axis J2 from the proximal portion to the distal portion in the second jaw 22. A jaw back surface (second jaw back surface) 27 facing the jaw open direction (second jaw open direction) is formed on the outer surface of the second jaw 22 by the support member 31. In the second jaw 22, the receiving member 32 is fixed to the jaw close direction side of the support member 31. The receiving member 32 is made of an electrically insulating material. The receiving member 32 includes a base bottom surface 33 facing in the jaw close direction, and a protruding portion 35 protruding toward the jaw close direction of the second jaw 22 from the base bottom surface 33. The protruding portion 35 extends along the second jaw axis J2 in a range from the proximal portion to the distal portion in the second jaw 22. Here, the outer surface of the second jaw 22 is a surface exposed to the outside in the second jaw 22.

The second jaw 22 includes an electrode member (second electrode member) 36 fixed to the receiving member 32 on the base bottom surface 33. The electrode member 36 is fixed to the base bottom surface 33 of the receiving member 32 from the jaw close direction side of the second jaw 22. The electrode member 36 is made of an electrically conductive material. The electrode member 36 extends along the second jaw axis J2 from in the range the proximal portion to the distal portion in the second jaw 22, and is formed into a ring shape surrounding the protruding portion 35 of the receiving member 32.

One end of an electric power supply line (second high-frequency electric power supply line) 37 formed from, for example, an electric wire is connected to the proximal portion of the electrode member 36. The electric power supply line 37 extends through the space between the shaft 5 and the rod 25, an inside of the cylindrical case portion 6, and an inside of the cable 11, and has the other end connected to the high-frequency energy source 13 of the energy source unit 10. High-frequency electric power output from the high-frequency energy source 13 is supplied to the electrode member 36 of the second jaw 22 through the electric power supply line 37. When the electric power is supplied to the electrode member 36, the electrode member 36 functions as one electrode (second electrode) of the high-frequency electric power. Because the receiving member 32 is made of the electrically insulating material, no high-frequency electric power is supplied (transmitted) to the support member 31 and the receiving member 32.

As shown in FIG. 3, in the present embodiment, a treatment surface (second treatment surface) 28 opposed to the first jaw 21 is formed in the outer surface of the second jaw 22 by the protruding portion 35 of the receiving member 32 and the electrode member 36. The treatment surface (second treatment surface) 28 is a part of the outer surface of the second jaw 22, and faces the jaw close direction (second jaw close direction) of the second jaw 22.

FIG. 4 is a diagram showing the first jaw 21 that is disassembled into components. As shown in FIG. 2 to FIG. 4, the first jaw 21 includes a support member (first support member) 41 attached to the shaft 5 and the rod 25, and a heat insulating member 42 fixed to the support member 41. The support member 41 and the heat insulating member 42 extend along the first jaw axis J1 in a range from the proximal portion to the distal portion in the first jaw 21. A jaw back surface (first jaw back surface) 51 facing the jaw open direction (first jaw open direction) is formed on the outer surface of the first jaw 21 by the support member 41. In the first jaw 21, the heat insulating member 42 is fixed to the jaw close direction side of the support member 41. The heat insulating member 42 is made of an electrically insulating material. Here, the outer surface of the first jaw 21 is a surface exposed to the outside in the first jaw 21.

In the first jaw 21, a blade (electrode member) 43 is fixed to the jaw close direction side (first jaw close direction side) of the heat insulating member 42. The blade 43 is made of an electrically conductive material having high heat transference. A cavity 45 is formed between the heat insulating member 42 and the blade 43 in the jaw open direction (open direction) and the jaw close direction (close direction). The cavity 45 is surrounded by the heat insulating member 42 and the blade 43. In the present embodiment, a treatment surface (first treatment surface) 52 is formed by the blade 43 in a position on the outer surface of the first jaw 21 to face the treatment surface (second treatment surface) 28 of the second jaw 22. The treatment surface (first treatment surface) 52 is a part of the outer surface of the first jaw 21, and faces the jaw close direction (first jaw close direction) of the first jaw 21.

One end of an electric power supply line (first high-frequency electric power supply line) 53 formed from, for example, an electric wire is connected to the proximal portion of the blade (cutting portion) 43. The electric power supply line 53 extends through the space between the shaft 5 and the rod 25, the inside of the cylindrical case portion 6, and the inside of the cable 11, and has the other end connected to the high-frequency energy source 13 of the energy source unit 10. High-frequency electric power (high-frequency electric energy) output from the high-frequency energy source 13 is supplied to the blade 43 of the first jaw 21 through the electric power supply line 53. When the electric power is supplied to the blade 43, the blade 43 functions as an electrode (first electrode) of the high-frequency electric power different in electric potential from the electrode member 36. Because the heat insulating member 42 is made of the electrically insulating material, no high-frequency electric power is supplied (transmitted) to the support member 41 and the heat insulating member 42.

An abutting surface (abutting portion) 55 which can abut the protruding portion 35 of the receiving member 32 in a state where the space between the first jaw 21 and the second jaw 22 is closed is provided on the treatment surface (first treatment surface) 52 formed by the blade 43. Therefore, a receiving surface 38 to receive the abutting surface 55 is formed in the receiving member 32. The receiving surface 38 is a part of the treatment surface (grasping surface) 28, and is formed from only the receiving member 32. When the space between the first jaw 21 and the second jaw 22 is closed in a state no treated target is present between the first jaw 21 and the second jaw 22, the abutting surface 55 abuts the receiving surface 38. In a state where the abutting surface 55 is in abutment with the receiving surface 38, the blade 43 does not contact the electrode member 36 of the second jaw 22, and there is a gap between the blade 43 and the electrode member 36. This prevents the contact between the electrode member 36 of the second jaw 22 and the blade 43 of the first jaw 21 that are different in electric potential from each other.

One of the jaw width directions of the first jaw 21 is a first jaw width direction (direction of an arrow W1 in FIG. 3), and the direction opposite to the first jaw width direction is a second jaw width direction (direction of an arrow W2 in FIG. 3). In the treatment surface (first treatment surface) 52 of the first jaw 21, an inclined surface (first inclined surface) 57A is provided on the first jaw width direction side of the abutting surface 55, and an inclined surface (second inclined surface) 57B is provided on the second jaw width direction side of the contact surface 55. In the inclined surface (separation portion) 57A, the distance from the treatment surface (grasping surface) 28 of the second jaw 22 decreases toward the second jaw width direction. In the inclined surface (separation portion) 57B, the distance from the treatment surface 28 of the second jaw 22 decreases toward the first jaw width direction. The blade 43 is formed into a shape such that the abutting surface 55 protrudes toward the second jaw 22 (first jaw close direction side) from the inclined surfaces 57A and 57B.

In the first jaw 21, a heating portion 40 is provided in the cavity 45 between the heat insulating member 42 and the blade 43. The heating portion 40 includes a heating wire (heater wire) 50 which is a heating element. The heating portion 40 is fixed to the heat insulating member 42, and also fixed to the blade 43. The exterior of the heating portion 40 is made of an electrically insulating material. Thus, the high-frequency electric power supplied to the blade 43 is not supplied to the heating wire 50. The heating portion 40 (the heating wire 50) is mounted between a mounting surface 46 of the heat insulating member 42 and a mounting surface 47 of the blade 43. That is, the heating portion 40 including the heating wire 50 is mounted on the mounting surfaces (contact surfaces) 46 and 47, and the heating portion 40 is in contact with the mounting surfaces 46 and 47. When the heating portion 40 (the heating wire 50) is provided in one of the two grasping portions (21 and 22), one of the grasping portions provided with the heating portion 40 is the first jaw (first grasping portion) 21, and the other one that is not provided with the heating portion 40 is the second jaw (second grasping portion) 22. In the first jaw 21 which is a heating jaw (heating grasping portion), only one heating wire 50 is provided, and no more than one heating wire is provided.

Figure 5:
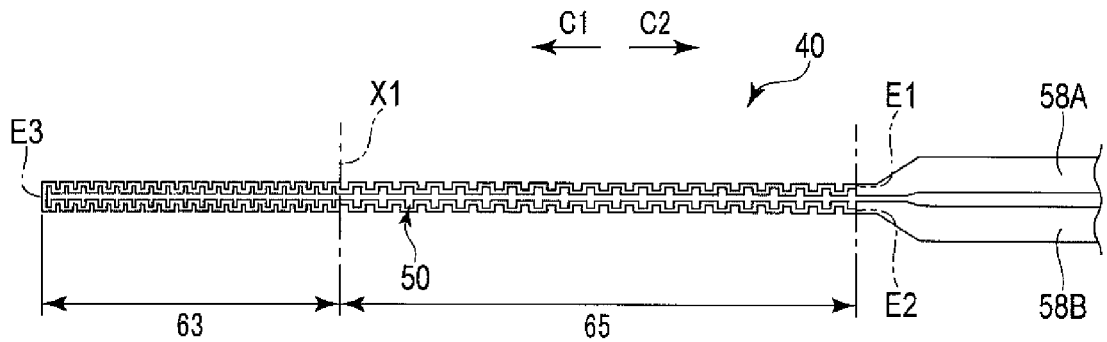
FIG. 5 is a schematic diagram showing the configuration of a heating wire (heating portion) according to the first embodiment.

FIG. 5 is a diagram showing the configuration of the heating wire 50 (heating portion 40). As shown in FIG. 4 and FIG. 5, the heating wire 50 has a first extending end E1 and a second extending end E2 which are both ends of the heating wire 50 in the extending direction, and continues without branching from the first extending end E1 to the second extending end E2. That is, the heating wire 50 continues without branching from the first extending end E1 which is one end to the second extending end E2 which is the other end in the extending direction. The first extending end E1 and the second extending end E2 are located in the proximal portion of the first jaw (heating jaw) 21. The heating wire 50 also has a turn position E3 between the first extending end E1 and the second extending end E2. The turn position E3 is located in the distal portion of the first jaw 21. The heating wire 50 extends toward the distal portion side (jaw distal direction) from the first extending end E1 to the turn position E3, and extends toward the proximal portion side (jaw proximal direction) from the turn position E3 to the second extending end E2. Therefore, the turn position E3 is a substantially intermediate position between the first extending end E1 and the second extending end E2. Because the heating wire 50 extends as described above, the heating wire 50 is provided in a range from the proximal portion to the distal portion in the jaw longitudinal directions in the first jaw (heating grasping portion) 21. Thus, in the first jaw 21, the heating portion 40 (the heating wire 50) is mounted on the mounting surfaces (the mounting surface 46 of the heat insulating member 42 and the mounting surface 47 of the blade 43) in a range from the proximal portion to the distal portion in the jaw longitudinal directions.

One end of an electric power supply line (first heat electric power supply line) 58A formed from, for example, an electric wire is connected to the first extending end E1 of the heating wire 50. One end of an electric power supply line (second heat electric power supply line) 58B formed from, for example, an electric wire is connected to the second extending end E2 of the heating wire 50. The electric power supply lines 58A and 58B extend through the space between the shaft 5 and the rod 25, the inside of the cylindrical case portion 6, and the inside of the cable 11, and have the other ends connected to the heat energy source 12 of the energy source unit 10. Electric power (heat electric energy) output from the heat energy source (energy source) 12 is supplied to the heating wire 50 of the first jaw 21 through the electric power supply lines 58A and 58B. When the electric power is supplied to the heating wire 50, a voltage (electric potential difference) is produced between the first extending end E1 and the second extending end E2, and an electric current flows through the heating wire (heater wire) 50. In this instance, in the heating wire 50, the electric current flows between the first extending end E1 and the second extending end E2 without shunt current. When the electric current flows through the heating wire 50, heat is generated due to thermal resistance of the heating wire 50. In this instance, heat is generated over the entire length of the heating wire 50 from the first extending end E1 to the second extending end E2 in the extending direction of the heating wire 50.

The heat generated in the heating wire 50 is transmitted to the treatment surface (first treatment surface) 52 of the blade 43 via the mounting surface 47. The treated target is treated by the heat transmitted to the treatment surface (first treatment surface) 52. In the present embodiment, a temperature sensor (thermocouple) 61 which is a temperature detection section configured to detect the temperature of the distal portion of the treatment surface 52 is attached to the blade 43. One end of each of signal lines 62A and 62B formed from, for example, electric signal wires is connected to the temperature sensor 61. The signal lines 62A and 62B extend through the space between the shaft 5 and the rod 25, the inside of the cylindrical case portion 6, and the inside of the cable 11, and have the other ends connected to the control section 15 of the energy source unit 10. A detection signal based on the detection result in the temperature sensor 61 is transmitted to the control section 15 via the signal lines 62A and 62B. The control section 15 controls the output state of the electric power from the heat energy source 12 on the basis of the detected temperature of the distal portion of the treatment surface 52.

The heating wire 50 includes a first heating region 63, and a second heating region 65 provided on the proximal portion side (jaw proximal direction side) of the first heating region 63. In the present embodiment, the extending state of the heating wire 50 changes between the first heating region 63 and the second heating region 65. That is, the extending state of the heating wire 50 changes at a boundary position X1 of the first heating region 63 and the second heating region 65. The first heating region 63 is provided in a range from the distal portion to the boundary position X1 in the first jaw 21, and the second heating region 65 is provided in a range from the proximal portion to the boundary position X1 in the first jaw 21. Therefore, the first extending end E1 and the second extending end E2 of the heating wire 50 are located in the second heating region 65, and the turn position E3 of the heating wire 50 is located in the first heating region 63. In one example, the boundary position X1 corresponds to an intermediate position in the longitudinal direction of the first jaw (heating grasping portion) 21. In another example, the boundary position X1 is located on the proximal portion side apart from the distal end of the first jaw 21 by the dimension of one third of the entire length of the first jaw (heating jaw) 21 in the longitudinal direction.

Figure 6:
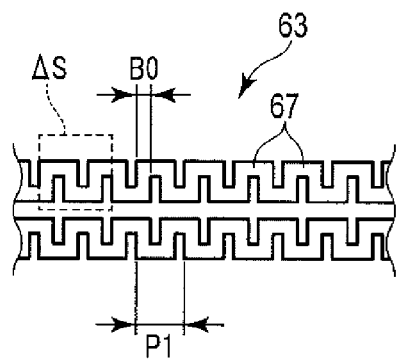
FIG. 6 is a schematic diagram showing an extending state of the heating wire according to the first embodiment in a first heating region.
Figure 7:
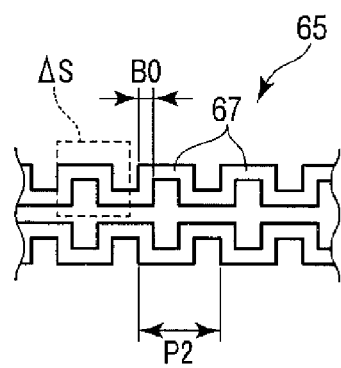
FIG. 7 is a schematic diagram showing an extending state of the heating wire according to the first embodiment in a second heating region.

FIG. 6 shows the extending state of the heating wire 50 in the first heating region 63. FIG. 7 shows the extending state of the heating wire 50 in the second heating region 65. As shown in FIG. 6 and FIG. 7, in the present embodiment, the wire width of the heating wire 50 is B0 and uniform, and is, for example, 0.1 mm in the first heating region 63 and the second heating region 65. The wire thickness of the heating wire 50 is also uniform in the first heating region 63 and the second heating region 65. Here, the wire width of the heating wire 50 is a dimension of the heating wire 50 in a direction (i.e. the width direction of the heating wire 50) which is perpendicular to the extending direction of the heating wire 50 and which is parallel to the mounting surface 46 of the heat insulating member 42 (the mounting surface 47 of the blade 43). The wire thickness of the heating wire 50 is a dimension of the heating wire 50 in a direction (i.e. the thickness direction of the heating wire 50) which is perpendicular to the extending direction of the heating wire 50 and which is parallel to the mounting surface 46 of the heat insulating member 42 (the mounting surface 47 of the blade 43).

In the heating wire 50, extending patterns 67 repetitively continue. In the present embodiment, a pitch (repetition interval) P1 of the extending patterns 67 in the first heating region 63 is smaller than a pitch (repetition interval) P2 of the extending patterns 67 in the second heating region 65. For example, the pitch P1 of the extending patterns 67 in the first heating region 63 is 0.3 mm, whereas the pitch P2 of the extending patterns 67 in the second heating region 65 is 0.5 mm.

Because the pitch P1 of the extending patterns 67 is smaller in the first heating region 63, the number density (number) of the extending patterns 67 in the first heating region 63 per unit area ΔS of the mounting surface 47 of the blade 43 is higher than the number density (number) of the extending patterns 67 in the second heating region 65 per unit area ΔS of the mounting surface 47 of the blade 43. Thus, the path length along the extending direction of the heating wire 50 per unit area ΔS of the mounting surface 47 of the blade 43 (the mounting surface 46 of the heat insulating member 42) is longer in the first heating region 63 (the distal portion of the first jaw 21) than in the second heating region 65 (the proximal portion of the first jaw 21). In the first heating region 63, the path length of the heating wire 50 is longer, so that the calorific value from the heating wire 50 per unit area ΔS of the mounting surface 47 is higher than in the second heating region 65. That is, in the first jaw (heating grasping portion) 21, the calorific value from the heating wire 50 per unit area ΔS of the mounting surface 47 (the mounting surface 46) is higher in the distal portion than in the proximal portion in a state where heat is generated from the heating wire 50 (heating portion 40). In the example in which the boundary position X1 of the first heating region 63 and the second heating region 65 corresponds to the intermediate position in the longitudinal direction of the first jaw (heating portion) 21, the calorific value from the heating wire 50 per unit area ΔS of the mounting surface (46 or 47) is higher in the region (first heating region 63) located on the distal portion side with respect to the intermediate position than in the region (second heating region 65) located on the proximal portion side with respect to the intermediate position of the first jaw 21. In the first jaw 21, the calorific value from the heating wire 50 per unit area ΔS is higher in the distal portion than in the proximal portion, so that the amount of heat transfer from the heating portion 40 to the treatment surface (first treatment surface) 52 is greater in the distal portion than in the proximal portion.

Next, functions and advantageous effects of the grasping treatment unit 20, the grasping treatment instrument 2, and the grasping treatment system 1 according to the present embodiment are described. When a treated target such as a living tissue is treated by use of the grasping treatment system 1, the grasping treatment unit 20 (the first jaw 21 and the second jaw 22) is inserted into the body, and the treated target is disposed between the first jaw 21 and the second jaw 22. The movable handle 8 is then moved to close relative to the fixed handle 7, and an open-or-close operation of the grasping treatment unit 20 is input. As a result, the space between the first jaw 21 and the second jaw 22 is closed, and the treated target is grasped between the first jaw 21 and the second jaw 22. In a state where the treated target is grasped, an energy operation is input in the energy operation input portion 16. Accordingly, under the control of the control section 15, electric power (heat electric energy) is output from the heat energy source 12, and high-frequency electric power (high-frequency electric energy) is output from the high-frequency energy source 13.

When the electric power is supplied to the heating wire 50 from the heat energy source 12, heat is generated in the heating wire 50, and the generated heat is transmitted to the treatment surface (first treatment surface) 52 formed in the blade 43 of the first jaw 21. As a result, the treated target which is in contact with the treatment surface (first treatment surface) 52 is burned, and cut open. Here, when the calorific value is reduced in the heating wire 50 to reduce the temperature of the treatment surface 52, the treated target is coagulated. The calorific value in the heating wire 50 can be adjusted by the adjustment of the electric power supplied to the heating wire 50. When the treated target is cut open, the temperature of the treatment surface 52 is about 230° C. to 350° C., and is preferably about 250° C. to 300° C. When the treated target is coagulated, the temperature of the treatment surface 52 is about 200° C. Therefore, in a treatment using the heat generated in the heating wire 50, the temperature of the treatment surface 52 is about 200° C. or more and 350° C. or less.

When high-frequency electric power is supplied to the electrode member 36 of the second jaw 22 and the blade 43 of the first jaw 21 from the high-frequency energy source 13, the electrode member 36 and the blade 43 function as electrodes that are different in electric potential from each other. As a result, a high-frequency current flows between the electrode member 36 and the blade 43 through the treated target (living tissue) grasped between the first jaw 21 and the second jaw 22. The high-frequency current denatured the treated target, and accelerates coagulation.

The grasping treatment instrument 2 performs the treatment (small-bite method) wherein the respective distal portions of the first jaw 21 and the second jaw 22 (e.g. ranges of the first jaw 21 and the second jaw 22 which are the dimension of one third of the entire length from the distal ends in the jaw longitudinal directions) are only brought into contact with the treated target, and the treated target is repetitively cut open by use of heat. In this treatment, only the distal portion in the first jaw (heating jaw) 21 provided with the heating wire 50 (heating portion 40) contacts the treated target. Thus, in the first jaw 21, heat is released to the treated target from only the outer surface of the distal portion (the distal portion of the treatment surface 52), and the heat release amount from the distal portion of the treatment surface (grasping surface) 52 increases.

In the first jaw (heating grasping portion) 21 according to the present embodiment, the path length along the extending direction of the heating wire 50 per unit area ΔS of the mounting surface 47 of the blade 43 (the mounting surface 46 of the heat insulating member 42) is longer in the distal portion (the first heating region 63) than in the proximal portion (the second heating region 65). Thus, in the first jaw (heating grasping portion) 21, the calorific value from the heating wire 50 per unit area ΔS of the mounting surface 47 (the mounting surface 46) is higher in the distal portion than in the proximal portion in a state where heat is generated from the heating wire 50. Therefore, the amount of heat transfer from the heating portion 40 to the treatment surface (first treatment surface) 52 is greater in the distal portion than in the proximal portion. Consequently, even in the treatment (small-bite method) in which the heat release amount in the distal portion of the first jaw 21 is greater, the amount of heat transfer to the distal portion of the treatment surface (first treatment surface) 52 is greater, so that the decrease of temperature of the distal portion of the treatment surface 52 (the distal portion of the first jaw 21) is inhibited. Because the temperature of the distal portion of the treatment surface (first treatment surface) 52 is maintained without being decreased, the efficiency of cutting of the treated target is ensured, and the treatment can be rapidly conducted.

In the present embodiment, the calorific value from the heating wire 50 in the distal portion of the first jaw 21 increases without increasing the electric power to the heating wire 50. That is, in a state where the calorific value from the heating wire 50 is higher in the distal portion of the first jaw 21, a low calorific value from the heating wire 50 is maintained in the proximal portion of the first jaw 21. Therefore, in the treatment (small-bite method), excessive increase of the temperature in the proximal portion of the first jaw 21 which does not contact the treated target (i.e. which does not release heat to the treated target) is inhibited.

In the present embodiment, it is possible to increase the calorific value from the heating wire 50 in the distal portion of the first jaw 21 (the first heating region 63) alone merely by passing an electric current through only one heating wire 50 provided in the first jaw (heating jaw) 21. For example, more than one heating wire (heating element) are provided in the first jaw (21), and the state of supply of electric power through the electric power supply line corresponding to each heating wire is controlled, so that the calorific value (temperature) can be higher in the distal portion alone in the first jaw (21). However, in this case, the configurations of wiring lines and other between the heating elements and the electric power source increase in complexity, and the control of the output state of electric power from the electric power source also increases in complexity. That is, in the present embodiment, the calorific value from the heating wire 50 can be increased in the distal portion of the first jaw 21 (the first heating region 63) alone with a simple configuration and by simple output control of electronic power.

In the present embodiment, the temperature of the distal portion of the treatment surface (first treatment surface) 52 is detected by the temperature sensor 61, and the control section 15 controls the output state of electric power from the heat energy source 12 on the basis of the detection result of the temperature. Thus, it is possible to easily adjust the temperature of the distal portion of the treatment surface (grasping surface) 52 to a desired temperature (e.g. 250° C.) suited to the treatment (small-bite method) by controlling the output state of electric power from the heat energy source 12. A memory (not shown) or the like may be provided in the energy source unit 10 so as to store the desired temperature, and the relation of electric power and the temperature of the distal portion of the treatment surface 52.

(Modifications)

Figure 9:
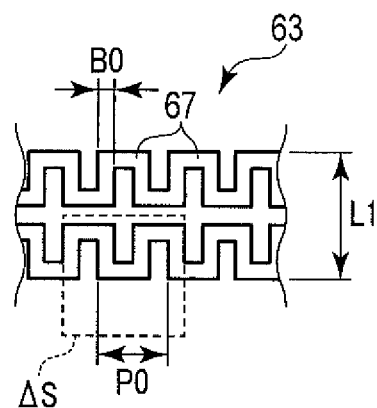
FIG. 9 is a schematic diagram showing an extending state of the heating wire according to the first modification in the first heating region.
Figure 10:
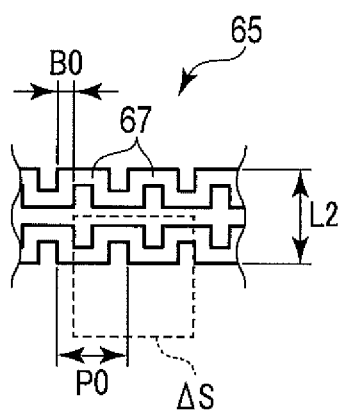
FIG. 10 a schematic diagram showing an extending state of the heating wire according to the first modification in the second heating region.

Although the pitch (repetition interval) P1 of the extending patterns 67 in the first heating region 63 is smaller than the pitch (repetition interval) P2 of the extending patterns 67 in the second heating region 65 in the first embodiment, it is not limited to this. For example, a first modification is described with reference to FIG. 8 to FIG. 10. FIG. 8 is a diagram showing the configuration of the heating wire 50 (heating portion 40) according to the present modification. FIG. 9 shows an extending state of the heating wire 50 in the first heating region 63 according to the present modification. FIG. 10 shows an extending state of the heating wire 50 in the second heating region 65 according to the present modification. As shown in FIG. 8 to FIG. 10, in the present modification as well as in the first embodiment, the wire width of the heating wire 50 is B0 and uniform, and is, for example, 0.1 mm in the first heating region 63 and the second heating region 65. The wire thickness of the heating wire 50 is also uniform in the first heating region 63 and the second heating region 65.

In the heating wire 50, the extending patterns 67 repetitively continue. However, in the present modification different from the first embodiment, the pitch of the extending patterns 67 in the first heating region 63 and the pitch of the extending patterns 67 in the second heating region 65 are P0 and uniform, and is, for example, 0.4 mm. In the present modification, the dimensions of the first heating region 63 and the second heating region 65 in the jaw width directions (directions of an arrow W1 and an arrow W2 in FIG. 8) of the first jaw (heating jaw) 21 differ from each other. That is, in the present modification, a dimension L1 of the first heating region 63 in the jaw width directions is greater than a dimension L2 of the second heating region 65 in the jaw width directions. For example, the dimension L1 of the first heating region 63 in the jaw width directions is 0.8 mm, whereas the dimension L2 of the second heating region 65 in the jaw width directions is 0.6 mm.

Because the dimension of the first heating region 63 in the jaw width directions is greater, the path length along the extending direction of the heating wire 50 per unit area ΔS of the mounting surface 47 of the blade 43 (the mounting surface 46 of the heat insulating member 42) is longer in the first heating region 63 (the distal portion of the first jaw 21) than in the second heating region 65 (the proximal portion of the first jaw 21). In the first heating region 63, the path length of the heating wire 50 is longer, so that the calorific value from the heating wire 50 per unit area ΔS of the mounting surface 47 is higher than in the second heating region 65. Therefore, in the present modification as well as in the first embodiment, in the first jaw (heating grasping portion) 21, the calorific value from the heating wire 50 per unit area ΔS of the mounting surface 47 (the mounting surface 46) is higher in the distal portion than in the proximal portion in a state where heat is generated from the heating wire 50.

In a second modification shown in FIG. 11 to FIG. 13, the path length along the extending direction of the heating wire 50 per unit area ΔS of the mounting surface 47 of the blade 43 (the mounting surface 46 of the heat insulating member 42) is uniform in the first heating region 63 and the second heating region 65. Therefore, the pitch of the extending patterns 67 is P0 and uniform, and is, for example, 0.4 mm in the first heating region 63 and the second heating region 65. The dimension of the first heating region 63 in the jaw width directions is the same as the dimension of the second heating region 65 in the jaw width directions. FIG. 11 is a diagram showing the configuration of the heating wire 50 (heating portion 40) according to the present modification. FIG. 12 shows an extending state of the heating wire 50 in the first heating region 63 according to the present modification. FIG. 13 shows an extending state of the heating wire 50 in the second heating region 65 according to the present modification. However, in the present modification, a wire width B1 of the heating wire 50 in the first heating region 63 is smaller than a wire width B2 of the heating wire 50 in the second heating region 65. For example, the wire width B1 of the heating wire 50 in the first heating region 63 is 0.05 mm, whereas the wire width B2 of the heating wire 50 in the second heating region 65 is 0.1 mm. In the present modification, the wire thickness of the heating wire 50 is uniform in the first heating region 63 and the second heating region 65. Thus, the sectional area perpendicular to the extending direction of the heating wire 50 is smaller in the first heating region 63 (the distal portion of the first jaw 21) than in the second heating region 65 (the proximal portion of the first jaw 21). In the first heating region 63, the sectional area of the heating wire 50 is smaller, so that the calorific value from the heating wire 50 per unit area ΔS of the mounting surface 47 is higher than in the second heating region 65. Therefore, in the present modification as well as in the first embodiment, in the first jaw (heating jaw) 21, the calorific value from the heating wire 50 per unit area ΔS of the mounting surface 47 (the mounting surface 46) is higher in the distal portion than in the proximal portion in a state where heat is generated from the heating wire 50.

In a third modification shown in FIG. 14, a wire thickness T1 of the heating wire 50 in the first heating region 63 is smaller than a wire thickness T2 of the heating wire 50 in the second heating region 65. For example, the wire thickness T1 of the heating wire 50 in the first heating region 63 is 0.01 mm, whereas the wire thickness T2 of the heating wire 50 in the second heating region 65 is 0.02 mm. In the present modification, the wire width of the heating wire 50 is B0 and uniform, and is, for example, 0.1 mm in the first heating region 63 and the second heating region 65. In the present modification as well as in the second embodiment, the path length along the extending direction of the heating wire 50 per unit area ΔS of the mounting surface 47 of the blade 43 (the mounting surface 46 of the heat insulating member 42) is uniform in the first heating region 63 and the second heating region 65.

Because of the configuration described above, in the present modification as well as in the second embodiment, the sectional area perpendicular to the extending direction of the heating wire 50 is smaller in the first heating region 63 (the distal portion of the first jaw 21) than in the second heating region 65 (the proximal portion of the first jaw 21). In the first heating region 63, the sectional area of the heating wire 50 is smaller, so that the calorific value from the heating wire 50 per unit area ΔS of the mounting surface 47 is higher than in the second heating region 65. Therefore, in the present modification as well as in the first embodiment, in the first jaw (heating jaw) 21, the calorific value from the heating wire 50 per unit area ΔS of the mounting surface 47 (the mounting surface 46) is higher in the distal portion than in the proximal portion in a state where heat is generated from the heating wire 50.

In a fourth modification shown in FIG. 15, the path length along the extending direction of the heating wire 50 per unit area ΔS of the mounting surface 47 of the blade 43 (the mounting surface 46 of the heat insulating member 42) and the sectional area perpendicular to the extending direction of the heating wire 50 are uniform in the first heating region 63 and the second heating region 65. However, in the present modification, the material that forms the heating wire 50 varies between the first heating region 63 and the second heating region 65. That is, in the first jaw (heating grasping portion) 21, the electric resistance of the material forming the heating wire 50 is higher in the first heating region 63 (the distal portion) than in the second heating region 65 (the proximal portion). For example, the heating wire 50 is made of stainless steel in the second heating region 65, whereas the heating wire 50 is made of Nichrome higher in electric resistance than stainless steel in the first heating region 63. In the heating wire 50 shown in FIG. 15, the first heating region 63 is indicated by dotted hatching, and the second heating region 65 is indicated in a non-hatched plain form.

In the present modification, in the first heating region 63, the electric resistance of the heating wire 50 is higher, so that the calorific value from the heating wire 50 per unit area ΔS of the mounting surface 47 is higher than in the second heating region 65. Therefore, in the present modification as well as in the first embodiment, in the first jaw (heating jaw) 21, the calorific value from the heating wire 50 per unit area ΔS of the mounting surface 47 (the mounting surface 46) is higher in the distal portion than in the proximal portion in a state where heat is generated from the heating wire 50.

Although the extending state of the heating wire 50 and the sectional area of the heating wire 50 etc. change at the boundary position X1 of the first heating region 63 and the second heating region 65 in the embodiments and others described above, it is not limited to this. For example, as in a fifth modification shown in FIG. 16, a pitch (repetition interval) P of the extending patterns 67 may be gradually smaller (i.e. may gradually decrease) from the proximal portion (jaw proximal direction) toward the distal portion (jaw distal direction) in the heating wire 50 of the first jaw (heating jaw) 21. Although the heating wire 50 is shown in a line-shape in FIG. 16, the heating wire 50 has a wire width in the present modification as well as in the embodiments described above.

In the present modification, the pitch P of the extending patterns 67 may gradually decrease from the proximal portion toward the distal portion of the first jaw 21, so that the number density (number) of the extending patterns 67 of the second heating region 65 per unit area ΔS of the mounting surface 47 of the blade 43 gradually increases from the proximal portion toward the distal portion in the first jaw 21. Accordingly, in the heating wire 50 of the first jaw 21, the path length along the extending direction of the heating wire 50 per unit area ΔS of the mounting surface 47 of the blade 43 (the mounting surface 46 of the heat insulating member 42) gradually increases from the jaw proximal direction toward the jaw distal direction. Therefore, in the first jaw (heating grasping portion) 21, the calorific value from the heating wire 50 per unit area ΔS of the mounting surface 47 gradually increases (becomes gradually higher) from the proximal portion toward the distal portion. Owing to the configuration described above, in the present modification as well as in the first embodiment, in the first jaw (heating grasping portion) 21, the calorific value from the heating wire 50 per unit area ΔS of the mounting surface 47 (the mounting surface 46) is higher in the distal portion than in the proximal portion in a state where heat is generated from the heating wire 50.

One of the configurations of the heating wire 50 according to the first to fourth modifications may be applied so that in the first jaw (heating jaw) 21, the calorific value from the heating wire 50 per unit area ΔS of the mounting surface 47 (the mounting surface 46) may gradually increase from the proximal portion toward the distal portion. For example, when the configuration of the heating wire 50 according to the second modification is applied, the width of the heating wire 50 is gradually decreased from the proximal portion toward the distal portion in the first jaw (heating grasping portion) 21 so that the calorific value from the heating wire 50 per unit area ΔS of the mounting surface 47 gradually increases (becomes gradually higher) from the proximal portion toward the distal portion.

Figure 17:
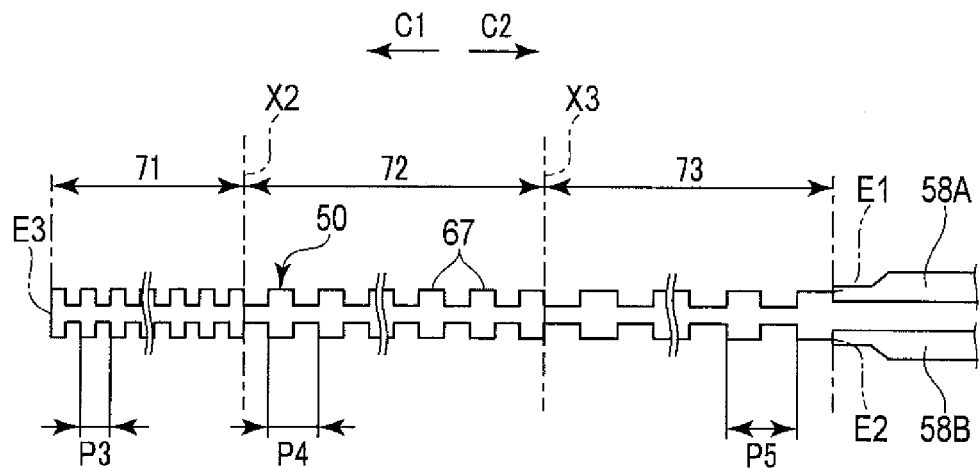
FIG. 17 is a schematic diagram showing the configuration of the heating wire according to a sixth modification.

As in a sixth modification shown in FIG. 17, the heating wire 50 may be divided in the jaw longitudinal directions (longitudinal directions) of the first jaw (heating jaw) 21 into three heating regions (regions) 71 to 73 different from each other in the calorific value from the heating wire 50 per unit area ΔS of the mounting surface 47 (the mounting surface 46). In the present modification, the first heating region 71 is located in the distal portion of the first jaw 21, and the second heating region 72 is continuous with the jaw proximal direction side of the first heating region 71. The third heating region 73 is continuous with the jaw proximal direction side of the second heating region 72, and is located in the proximal portion of the first jaw 21. Although the heating wire 50 is shown in a line-shape in FIG. 17, the heating wire 50 has a wire width in the present modification as well as in the embodiments described above.

In the present modification, the extending state of the heating wire 50 changes at a boundary position X2 of the first heating region 71 and the second heating region 72 and at a boundary position X3 of the second heating region 72 and the third heating region 73. That is, in the present modification, a pitch (repetition interval) P3 of the extending patterns 67 in the first heating region 71 is smaller than a pitch (repetition interval) P4 of the extending patterns 67 in the second heating region 72. The pitch (repetition interval) P4 of the extending patterns 67 in the second heating region 72 is smaller than a pitch (repetition interval) P5 of the extending patterns 67 in the third heating region 73.

Thus, in the present modification, the calorific value from the heating wire 50 per unit area ΔS of the mounting surface 47 (the mounting surface 46) is higher in the first heating region 71 than in the second heating region 72, and higher in the second heating region 72 than in the third heating region 73. That is, the calorific value from the heating wire 50 per unit area ΔS of the mounting surface 47 is higher in the regions located more distally (jaw distal direction side) among the three heating regions (regions) 71 to 73. Owing to the configuration described above, in the present modification as well as in the first embodiment, in the first jaw (heating jaw) 21, the calorific value from the heating wire 50 per unit area ΔS of the mounting surface 47 (the mounting surface 46) is higher in the distal portion than in the proximal portion in a state where heat is generated from the heating wire 50.

One of the configurations of the heating wire 50 according to the first to fourth modifications may be applied so that in the first jaw (heating jaw) 21, the calorific value from the heating wire 50 per unit area ΔS of the mounting surface 47 (the mounting surface 46) may be higher in the first heating region 71 than in the second heating region 72, and higher in the second heating region 72 than in the third heating region 73. For example, when the configuration of the heating wire 50 according to the second modification is applied, the width of the heating wire 50 is changed at the boundary position X2 of the first heating region 71 and the second heating region 72 and at the boundary position X3 of the second heating region 72 and the third heating region 73 so that the calorific value from the heating wire 50 per unit area ΔS of the mounting surface 47 may be higher in the first heating region 71 than in the second heating region 72, and higher in the second heating region 72 than in the third heating region 73.

The heating wire 50 may be divided in the jaw longitudinal directions (longitudinal directions) of the first jaw (heating jaw) 21 into four or more heating regions (regions) different from each other in the calorific value from the heating wire 50 per unit area ΔS of the mounting surface 47 (the mounting surface 46). In this case as well as in the sixth modification in which the heating wire 50 is divided into the three heating regions 71 to 73, the calorific value from the heating wire 50 per unit area ΔS of the mounting surface 47 is higher in the regions located more distally (jaw distal direction side) among the heating regions (regions).

Figure 18:
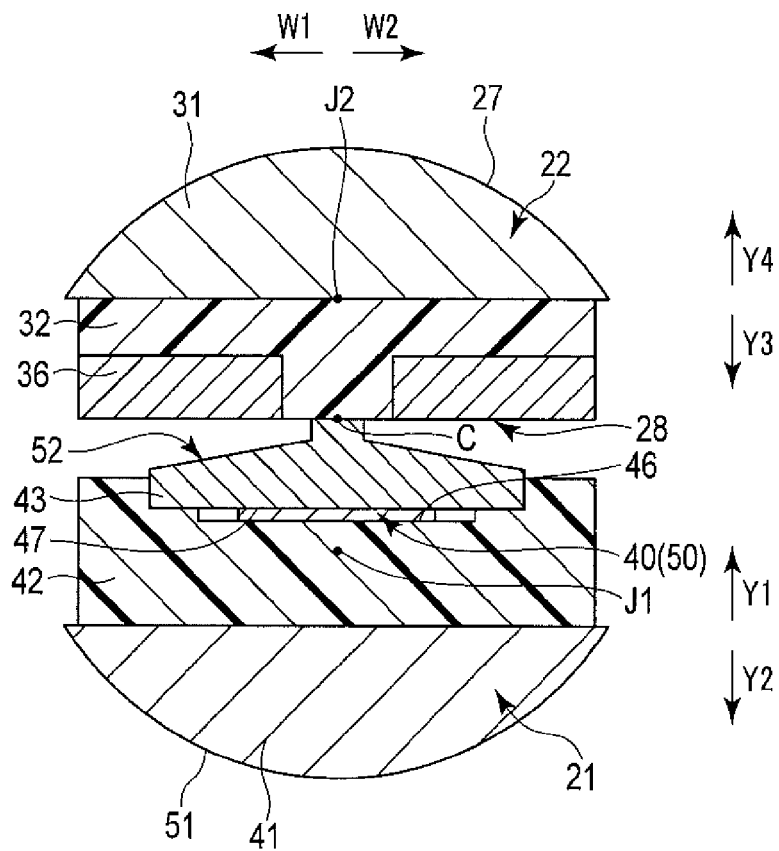
FIG. 18 is a sectional view schematically showing the first jaw and the second jaw according to the seventh modification in the section perpendicular to the longitudinal axis.

As in a seventh modification shown in FIG. 18, the first jaw (first grasping portion) 21 provided with the heating portion 40 may be fixed to the shaft 5. In the present modification, the second jaw 22 which is not provided with the heating portion 40 is rotatably attached to the shaft 5. As shown in FIG. 18, in the present modification as well as in the first embodiment, the second jaw 22 is formed from the support member 31, the receiving member 32, and the electrode member 36. The treatment surface (second treatment surface) 28 opposed to the first jaw 21 is formed by the receiving member 32 and the electrode member 36.

As in the first embodiment, the first jaw 21 is formed from the support member 41, the heat insulating member 42, the blade 43, and the heating portion 40. The treatment surface (first treatment surface) 52 facing the second jaw 22 is formed by the blade 43. In the present modification as well, only one heating wire 50 is provided in the first jaw (heating jaw) 21. As in the first embodiment, the heating wire 50 extends in the first jaw 21. Thus, in the present modification as well as in the first embodiment, in the first jaw 21 which is the heating grasping portion, the calorific value from the heating wire 50 per unit area ΔS of the mounting surface 47 (the mounting surface 46) is higher in the distal portion than in the proximal portion in a state where heat is generated from the heating wire 50. Therefore, the amount of heat transfer from the heating portion 40 to the treatment surface (first treatment surface) 52 is greater in the distal portion than in the proximal portion.

In a certain modification, both the first jaw 21 and the second jaw 22 are heating jaws each of which is provided with the heating portion (40). In this case, only one heating wire (50) is provided in each of the heating jaws (21 and 22). The heating wire (50) extends in each of the heating jaws (each of the first jaw 21 and the second jaw 22) as well as in the first jaw 21 according to the embodiments and others described above. Thus, in each of the heating jaws (21 and 22) as well as in the first jaw 21 according to the embodiments and others described above, the calorific value from the heating wire 50 per unit area ΔS of the mounting surface 47 (the mounting surface 46) is higher in the distal portion than in the proximal portion in a state where heat is generated from the heating wire 50.

In the embodiments and others described above, one (e.g. the second jaw 22) of the two jaws (21 and 22) is fixed to the shaft 5, and the other (e.g. the first jaw 21) of the two jaws (21 and 22) is rotatable relative to the shaft 5. However, it is not limited to this. In a certain modification, both the first jaw 21 and the second jaw 22 may be rotatably attached to the shaft 5. In this case, the rod 25 is moved along the longitudinal axis C so that both the first jaw 21 and the second jaw 22 rotate relative to the shaft 5. Consequently, in the grasping treatment unit 20, the space between the first jaw 21 and the second jaw 22 opens or closes.

Although the high-frequency energy source 13 is provided in the energy source unit 10 in the embodiments described above, it is not limited to this. That is, it is not necessary to supply high-frequency electric power to the first jaw 21 and the second jaw 22. Therefore, it is only necessary that the heating wire 50 be provided in at least the first jaw 21 which is one of the two grasping portions (21 and 22) and that the heat energy source 12 which outputs electric power to be supplied to the heating wire 50 be provided in the energy source unit 10.

In the embodiments and others (including the modifications) described above, the space between the first jaw (21) and the second jaw (22) is openable and closable in the grasping treatment unit (20), and the heating wire (50) is mounted in the first jaw (21) over the range from the proximal portion to the distal portion. The heating wire (50) continues without branching from the first extending end (E1) to the second extending end (E2), and heat is generated over the entire length from the first extending end (E1) to the second extending end (E2) when the electric current flows. In the heating portion (40), the calorific value per unit area is higher in the distal portion than in the proximal portion in the first jaw (21) in a state where heat is generated from the heating wire (50). Thus, on the treatment surface (52) provided in the first jaw (21) to face the second jaw (22), the amount of heat transfer from the heating portion (40) is greater in the distal portion than in the proximal portion.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A grasping treatment unit configured to grasp and treat a living tissue, the grasping treatment unit comprising:
    a first jaw which extends from a first proximal portion toward a first distal portion, and which has an outer surface exposed to an outside;
    a second jaw which extends from a second proximal portion toward a second distal portion, and which is openable and closable relative to the first jaw;
    a heating portion including a heating wire, the heating wire
        being disposed in a range from the first proximal portion to the first distal portion in the first jaw,
        continuing without branching from a first extending end of the heating wire, which is one end of the heating wire, to a second extending end of the heating wire, which is the other end in an extending direction of the heating wire, and
        being configured to generate heat over an entire length thereof from the first extending end to the second extending end when an electric current flows therethrough,
    the heating portion being higher in calorific value per unit area in the first distal portion than in the first proximal portion in the first jaw in a state where the heat is generated from the heating wire; and
    a blade which includes
        a treatment surface facing the second jaw on the outer surface of the first jaw, and in which an abutting portion protrudes toward the second jaw on the treatment surface, and
        an inclined surface,
        the treatment surface and the inclined surface being formed in at least the first distal portion on the treatment surface,
        the treatment surface being configured to treat the living tissue in a state where an amount of the heat transferred from the heating wire to the treatment surface is greater in the first distal portion than in the first proximal portion,
        the blade being configured to cut open the living tissue by the heat transmitted to the treatment surface.

2. The grasping treatment unit according to claim 1, wherein a temperature of the treatment surface in the state where the heat is generated in the heating wire is 200° C. or more and 350° C. or less.

3. The grasping treatment unit according to claim 1, wherein in the heating portion, a path length along the extending direction of the heating wire per unit area is longer in the first distal portion than in the first proximal portion in the first jaw.

4. The grasping treatment unit according to claim 1, wherein in the heating portion, a sectional area perpendicular to the extending direction of the heating wire is smaller in the first distal portion than in the first proximal portion in the first jaw.

5. The grasping treatment unit according to claim 1, wherein in the heating portion, an electric resistance of a material forming the heating wire is higher in the first distal portion than in the first proximal portion in the first jaw.

6. The grasping treatment unit according to claim 1, wherein in the heating portion, the calorific value of heat produced by the heating wire per unit area increases from the first proximal portion toward the first distal portion in the first jaw.

7. The grasping treatment unit according to claim 1, wherein when an intermediate position in a longitudinal direction is defined in the first jaw, the calorific value of heat produced by the heating wire per unit area is higher in a region located on a first distal portion side of the heating portion of the first jaw with respect to the intermediate position than in a region located on a first proximal portion side of the heating portion of the first jaw with respect to the intermediate position.

8. The grasping treatment unit according to claim 1, wherein the heating portion is divided in a longitudinal direction into three or more regions different from each other in their calorific value of heat produced by the heating wire per unit area, and
   among the three or more regions, the calorific value of heat produced by the heating wire per unit area of the region closest to the first distal portion of the first jaw is higher than the calorific value of the heat produced by the heating wire per unit area of the other regions, and the calorific value of heat produced by the heating wire per unit area of the region farthest from the first distal portion of the first jaw is lower than the calorific value of the heat produced by the heating wire per unit area of the other regions.

9. The grasping treatment unit according to claim 1, wherein
   the heating wire has a turn position between the first extending end and the second extending end,
   the first extending end and the second extending end of the heating wire are located in the first proximal portion in the first jaw,
   the turn position of the heating wire is located in the first distal portion in the first jaw, and
   when an intermediate position in a longitudinal direction is defined in the first jaw, the heating wire extends toward a first distal portion side of the first jaw with respect to the intermediate position from the first extending end to the turn position, and extends toward a first proximal portion side of the first jaw with respect to the intermediate position from the turn position to the second extending end.

10. A grasping treatment instrument comprising:
    the grasping treatment unit according to claim 1;
    a holding unit which is provided closer to a proximal end of the instrument than a distal end of the instrument so as to be closer to the proximal end of the instrument than the grasping treatment unit, and which is configured to be held; and
    an open-or-close operation input portion which is provided in the holding unit, and to which an open-or-close operation to open or close the space between the first jaw and the second jaw of the grasping treatment unit is input.

11. A grasping treatment system comprising:
    the grasping treatment unit according to claim 1; and
    an energy source which is configured to output electric power to be supplied to the heating wire through the first extending end and the second extending end, and which is configured to pass the electric current through the heating wire by outputting the electric power.

12. The grasping treatment system according to claim 11, further comprising:
    a temperature detection section which is configured to detect a temperature of the first distal portion of the treatment surface; and
    a control section which is configured to control an output state of the electric power from the energy source on the basis of the detected temperature of the first distal portion of the treatment surface so that the temperature of the first distal portion of the treatment surface reaches a desired temperature.

* * * * *